US009965945B2

(12) United States Patent
Grubis

(10) Patent No.: US 9,965,945 B2
(45) Date of Patent: May 8, 2018

(54) PATIENT MONITORING SYSTEM AND METHOD CONFIGURED TO SUPPRESS AN ALARM

(71) Applicant: General Electric Company, Schenectady, NY (US)

(72) Inventor: Matthew George Grubis, New Berlin, WI (US)

(73) Assignee: General Electric Company, Schenectady, NY (US)

( * ) Notice: Subject to any disclaimer, the term of this patent is extended or adjusted under 35 U.S.C. 154(b) by 0 days. days.

(21) Appl. No.: 15/282,441

(22) Filed: Sep. 30, 2016

(65) Prior Publication Data

US 2018/0096590 A1 Apr. 5, 2018

(51) Int. Cl.
*G08B 29/18* (2006.01)
*G06F 19/00* (2018.01)
*G08B 21/02* (2006.01)

(52) U.S. Cl.
CPC ....... *G08B 29/185* (2013.01); *G06F 19/3418* (2013.01); *G08B 21/02* (2013.01)

(58) Field of Classification Search
CPC .... G08B 29/185; G08B 21/02; G06F 19/3418
USPC ........................................................ 340/506
See application file for complete search history.

(56) References Cited

U.S. PATENT DOCUMENTS

| 4,803,625 | A | 2/1989 | Fu et al. |
| 7,034,692 | B2 | 4/2006 | Hickle |
| 9,055,925 | B2 | 6/2015 | Paquet et al. |
| 9,095,316 | B2 | 8/2015 | Welch et al. |
| 9,189,941 | B2 * | 11/2015 | Eschelman ............ A61B 5/746 |
| 9,380,983 | B2 | 7/2016 | Rath |
| 9,767,667 | B2 * | 9/2017 | Sullivan ............. G08B 21/0461 |
| 2004/0178910 | A1 * | 9/2004 | Egger .................... G08B 21/22 340/556 |
| 2009/0275807 | A1 | 11/2009 | Sitzman et al. |
| 2011/0009710 | A1 | 1/2011 | Kroeger et al. |

(Continued)

OTHER PUBLICATIONS

Murias et al.; Alarms: Transforming a Nuisance into a Reliable Tool; 20070; 8 Pages.

(Continued)

*Primary Examiner* — Hirdepal Singh
(74) *Attorney, Agent, or Firm* — Dean D. Small; The Small Patent Law Group, LLC

(57) ABSTRACT

Patient monitoring system includes a master unit. The master unit is configured to receive signal data of the patient from a plurality of acquisition devices. The master unit is also configured to receive a warning signal from a triggered acquisition device of the plurality of acquisition devices. The warning signal is communicated by the triggered acquisition device upon determining that corresponding physiological signals of the triggered acquisition device satisfy a designated condition. In response to receiving the warning signal from the triggered acquisition device, the master unit is configured to analyze the signal data from another acquisition device of the plurality of acquisition devices to determine whether the warning signal is clinically relevant or clinically irrelevant or unreliable. The master unit may permit a patient alarm or suppress the patient alarm based on the signal data from another acquisition device.

20 Claims, 3 Drawing Sheets

(56) References Cited

U.S. PATENT DOCUMENTS

| | | | |
|---|---|---|---|
| 2012/0078131 A1* | 3/2012 | Zong | A61B 5/746 600/513 |
| 2012/0239435 A1 | 9/2012 | Ennett et al. | |
| 2013/0237775 A1* | 9/2013 | Gross | A61B 5/0205 600/301 |
| 2014/0005502 A1* | 1/2014 | Klap | A61B 5/113 600/301 |
| 2014/0180711 A1* | 6/2014 | Kamen | G06Q 10/06 705/2 |
| 2015/0006088 A1* | 1/2015 | Eshelman | G06F 19/3406 702/19 |
| 2015/0164349 A1* | 6/2015 | Gopalakrishnan | A61B 5/02405 600/508 |
| 2015/0186608 A1* | 7/2015 | Fuller | G06F 19/3406 705/2 |
| 2015/0302726 A1* | 10/2015 | Treacy | G06F 19/327 340/502 |
| 2015/0310733 A1 | 10/2015 | Gross | |
| 2016/0080107 A1* | 3/2016 | Girouard | A61B 5/0004 600/546 |
| 2016/0093197 A1 | 3/2016 | See et al. | |
| 2016/0093205 A1* | 3/2016 | Boyer | A61B 5/02416 340/506 |
| 2016/0321904 A1* | 11/2016 | Johnson | G06F 19/3406 |
| 2017/0100048 A1* | 4/2017 | Hu | A61B 5/04012 |

OTHER PUBLICATIONS

Borges et al.; Sensor fusion methods for reducing false alarms in heart rate monitoring; Springer Science+Business Media; 2015; 9 Pages.

International Search Report and Written Opinion for PCT/US2017/054242, dated Jan. 2, 2018, 16 pages.

Sadr et al., "Reducing false arrhythmia alarms in the ICU using multimodal signals and robust QRS detection," Institute of Physics and Engineering in Medicine, 2016, 15 pages.

* cited by examiner

PATIENT MONITORING SYSTEM AND METHOD CONFIGURED TO SUPPRESS AN ALARM

BACKGROUND

The subject matter herein relates generally to a patient monitoring system and method, and more particularly, to a patient monitoring system and method that monitors multiple parameters to identify whether a health-related event that should be communicated to a healthcare provider has occurred.

Patient monitoring systems are configured to receive physiological signals from a patient, analyze the physiological signals, and communicate information to a healthcare provider so that the healthcare provider may assess the health status of a patient. The physiological signals may include signals that are indicative of, for example, a heart rate, blood pressure, or peripheral oxygen saturation (SpO2). Monitoring systems may include a plurality of acquisition devices that detect the physiological signals and an operator display that presents the information to the healthcare provider. The monitoring systems also include one or more alarms that are configured to alert the healthcare providers to certain events.

Known monitoring systems may automatically determine when a health-related event has occurred and provide an alarm (e.g., audio noise, flashing light or other visual event, tactile movement, etc.) that notifies the healthcare provider of the health-related event. Health-related events may be determined by monitoring one or more parameters. For example, a heart rate monitor (e.g., an acquisition device) may determine that the heart rate (e.g., the parameter) of the patient has exceeded a designated limit. When the heart rate exceeds the designated limit, the heart rate monitor may issue an alarm that brings the attention of the healthcare provider to the patient. In this example, the health-related event is the rapid heart rate. In some monitoring systems, the acquisition devices are configured to operate independently and provide an alarm when the parameter that is monitored by the sensor satisfies a designated condition. In some monitoring systems, a single acquisition device may detect multiple parameters and/or multiple types of physiological signals. The alarms for the respective parameters may be different from other alarms so that a healthcare provider can identify the parameter that triggered the alarm.

False alarms can frequently occur in which the physiological signals incorrectly indicate that a health-related event has occurred. In addition, alarms for individual parameters may indicate a more serious health-related event when, in fact, the actual clinical situation is not as severe or concerning. For example, a sensor of the acquisition device can become displaced during the day. Consequently, the physiological signals detected by the sensor may be inaccurate and lead to a false alarm. False alarms can be frustrating to a healthcare provider and can also distract a healthcare provider from other matters. Moreover, frequent false alarms, including alarms that indicate the clinical situation is more severe than it actually is, can cause alarm fatigue such that the healthcare provider may believe a valid alarm is only another false alarm. It would be desirable to reduce the number of false alarms issued by the monitoring system.

BRIEF DESCRIPTION

In an embodiment, a patient monitoring system is provided that includes a master unit having a processor configured to execute programmed instructions stored in memory. The master unit is configured to communicatively couple to a plurality of acquisition devices. The acquisition devices have sensors configured to detect physiological signals from a patient and device circuitry configured to determine whether the corresponding physiological signals satisfy a designated condition. The master unit, when executing the programmed instructions, is configured to receive signal data of the patient from the acquisition devices, wherein the signal data is based on the physiological signals detected by one or more of the sensors of the corresponding acquisition devices. The master unit is also configured to receive a warning signal from a triggered acquisition device of the plurality of acquisition devices. The warning signal is communicated by the triggered acquisition device upon determining that the corresponding physiological signals of the triggered acquisition device satisfy the designated condition. In response to receiving the warning signal from the triggered acquisition device, the master unit is configured to analyze the signal data from another acquisition device of the plurality of acquisition devices to determine whether the warning signal is clinically relevant or clinically irrelevant or unreliable. The master unit permits a patient alarm associated with the triggered acquisition device to issue after determining the warning signal is clinically relevant. The master unit suppresses the patient alarm associated with the triggered acquisition device after determining that the warning signal is clinically irrelevant or unreliable.

In some aspects, the system includes the plurality of acquisition devices. The triggered acquisition device may be configured to confirm that a communication line exists between the triggered acquisition device and the master unit. The triggered acquisition device may permit the patient alarm to issue or another alarm to issue after attempting to communicate the warning signal to the master unit and after determining that the communication line is disconnected.

In some aspects, the master unit may be configured to log the physiological signals of the triggered acquisition device when the warning signal was communicated and the signal data of the other acquisition device after determining that the warning signal is clinically irrelevant or unreliable.

In some aspects, the signal data of the other acquisition device at least one of: (a) is the same type of signal data communicated by the triggered acquisition device; (b) corresponds to a patient parameter that is substantially related to the patient parameter of the signal data communicated by the triggered acquisition device; or (c) provides an explanation as to why the signal data of the triggered acquisition device is clinically irrelevant or unreliable.

In some aspects, the signal data from the other acquisition device may have a signal quality index. The determination by the master unit as to whether the warning signal is clinically relevant or clinically irrelevant or unreliable may be based on the signal quality index of the other acquisition device. Optionally, the signal data from the triggered acquisition device may have a signal quality index. The determination by the master unit as to whether the warning signal is clinically relevant or clinically irrelevant or unreliable may be based on the signal quality indexes of the other acquisition device and the triggered acquisition device.

In some aspects, the determination by the master unit as to whether the warning signal is clinically relevant or clinically irrelevant or unreliable may be based on data from a clinical source. Optionally, the data from the clinical source changes the designated condition that was satisfied at the triggered acquisition device. For example, the master unit may apply a similar analysis to the signal data, but the designated condition is different due to the data from the clinical source.

In an embodiment, a method of monitoring a patient is provided. The method includes receiving signal data of a patient from a plurality of acquisition devices that are operably coupled to the patient. The signal data is based on physiological signals detected by the acquisition devices. The method also includes receiving a warning signal from a triggered acquisition device of the plurality of acquisition devices. The warning signal is communicated by the triggered acquisition device upon determining that the corresponding physiological signals of the triggered acquisition device satisfy the designated condition. The method also includes analyzing, in response to receiving the warning signal from the triggered acquisition device, the signal data from another acquisition device of the plurality of acquisition devices to determine whether the warning signal is clinically relevant or clinically irrelevant or unreliable. The method also includes permitting a patient alarm associated with the triggered acquisition device to issue after determining that the warning signal is clinically relevant or suppressing the patient alarm associated with the triggered acquisition device after determining that the warning signal is clinically irrelevant or unreliable.

In some aspects, the method may also include confirming, at the triggered acquisition device, that a communication line exists between the triggered acquisition device and a master unit. The method may include permitting the patient alarm to issue or another alarm to issue after attempting to communicate the warning signal to the master unit and after determining that the communication line is disconnected.

In some aspects, the method also includes logging the physiological signals of the triggered acquisition device when the warning signal was communicated and the signal data of the other acquisition device after determining that the warning signal is clinically irrelevant or unreliable.

In some aspects, the signal data from the other acquisition device may have a signal quality index. The determination as to whether the warning signal is clinically relevant or clinically irrelevant or unreliable may be based on the signal quality index of the other acquisition device.

In some aspects, the method also includes receiving data from a clinical source. The determination as to whether the warning signal is clinically relevant or clinically irrelevant or unreliable may be based on the data from a clinical source. Optionally, the data from the clinical source changes the designated condition that was satisfied at the triggered acquisition device.

In an embodiment, a patient monitoring system is provided. The patient monitoring system includes a master unit having a processor configured to execute programmed instructions stored in memory. The master unit is configured to communicatively couple to a plurality of acquisition devices. The acquisition devices have sensors configured to detect physiological signals from a patient and device circuitry configured to determine whether the corresponding physiological signals satisfy a designated condition. The master unit, when executing the programmed instructions, is configured to receive signal data of the patient from the acquisition devices. The signal data is based on the physiological signals detected by one or more of the sensors of the corresponding acquisition devices. The acquisition devices include a primary acquisition device and one or more secondary acquisition devices. The master unit is also configured to analyze the signal data of the primary acquisition device and at least one secondary acquisition device to determine whether a health-related event has been detected. The determination as to whether the health-related event has been detected includes determining whether the signal data from the primary acquisition device satisfies a designated condition associated with the health-related event. In response to determining that the signal data from the primary acquisition device satisfies the designated condition, the determination as to whether the health-related event has been detected also includes determining whether the signal data from the at least one secondary acquisition device indicates the signal data of the primary acquisition device is clinically relevant or clinically irrelevant or unreliable. A patient alarm is permitted to issue if the signal data from the at least one secondary acquisition device indicates the signal data of the primary acquisition device is clinically relevant. The patient alarm is suppressed from issuing if the signal data from the at least one secondary acquisition device indicates the signal data of the primary acquisition device is clinically irrelevant or unreliable.

In some aspects, the master unit may be configured to log the signal data of the primary acquisition device and the at least one secondary acquisition device when the signal data from the at least one secondary acquisition device indicates the signal data of the primary acquisition device is clinically irrelevant or unreliable.

In some aspects, the health related event is a first health-related event and the primary acquisition device is a first primary acquisition device. The master unit may also be configured to analyze the signal data of a different second primary acquisition device and at least one secondary acquisition device to determine whether a different second health-related event has been detected. Determining whether the second health-related event has been detected may include determining whether the signal data from the second primary acquisition device satisfies a designated condition associated with the second health-related event. In response to determining that the signal data from the second primary acquisition device satisfies the designated condition, the master unit may determine whether the signal data from the at least one secondary acquisition device indicates the signal data of the second primary acquisition device is clinically relevant or clinically irrelevant or unreliable. Optionally, the second primary acquisition device is one of the secondary acquisition devices that provides signal data to determine whether the first health-related event occurred.

In some aspects, the determination by the master unit as to whether the signal data from the primary acquisition device satisfies the designated condition associated with the health-related event is based on data from a clinical source. Optionally, the data from the clinical source changes the designated condition associated with the health-related event.

In an embodiment, a method of monitoring a patient is provided. The method includes receiving signal data of a patient from a plurality of acquisition devices that are operably coupled to the patient. The signal data is based on physiological signals detected by the acquisition devices. The method also includes analyzing the signal data of the primary acquisition device and at least one secondary acquisition device to determine whether a health-related event has been detected. Determining whether the health-related event has been detected includes determining whether the signal data from the primary acquisition device satisfies a designated condition associated with the health-related event. In response to determining that the signal data from the primary acquisition device satisfies the designated condition, the method also includes determining whether the signal data from the at least one secondary acquisition device indicates the signal data of the primary acquisition device is clinically relevant or clinically irrelevant or unreliable. The method also includes permitting a patient alarm to issue if the signal data from the at least one secondary acquisition device indicates the signal data of the primary acquisition device is clinically relevant or suppressing the patient alarm if the signal data from the at least one secondary acquisition device indicates the signal data of the primary acquisition device is clinically irrelevant or unreliable.

DETAILED DESCRIPTION

Figure 1:
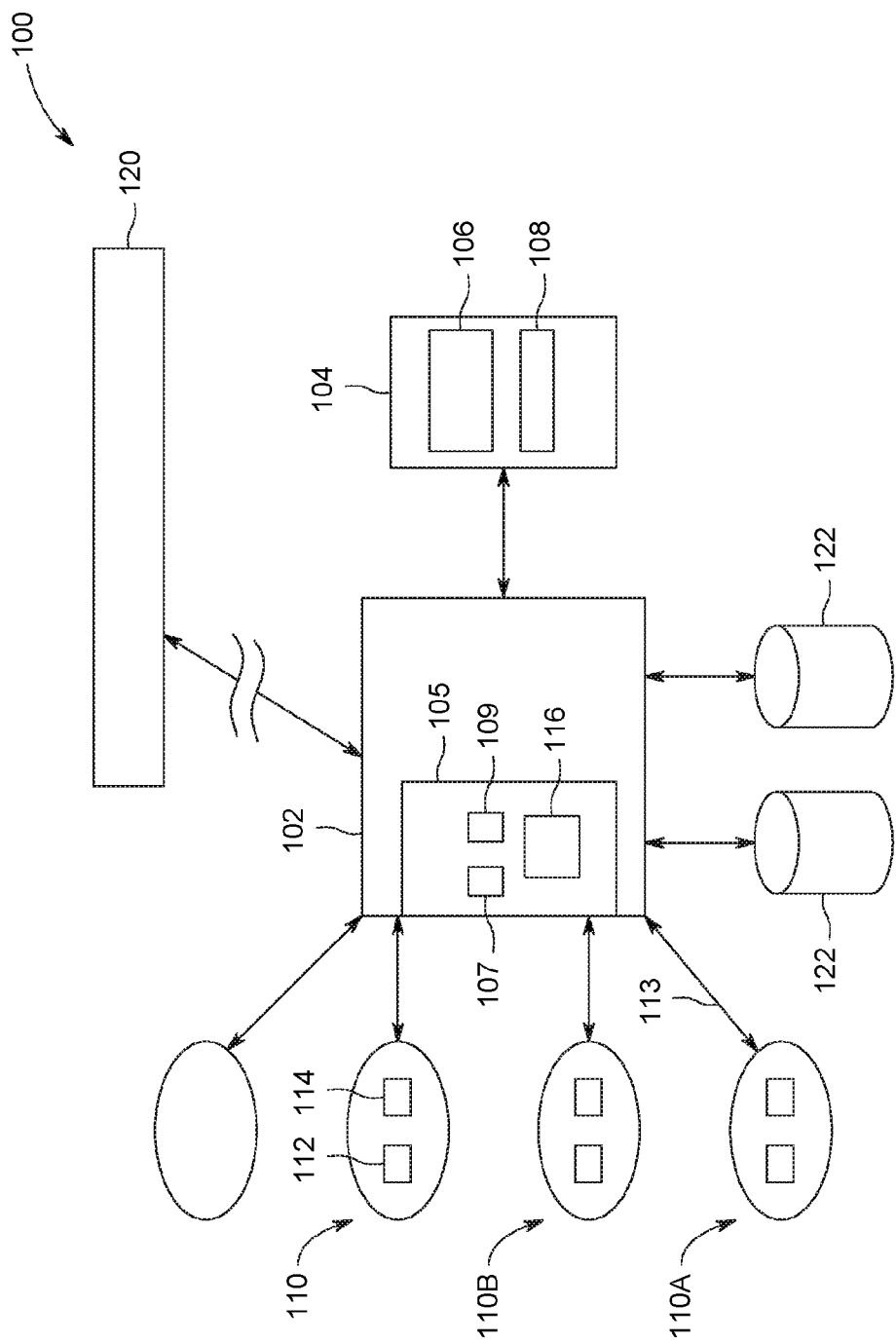
FIG. 1 is a block diagram of an exemplary system for displaying waveform information in accordance with one embodiment.

Embodiments set forth herein are configured to analyze physiological signals to determine whether to issue a patient alarm to a healthcare provider so that the healthcare provider may attend to the patient or make a decision about the patient. At least one technical effect of various embodiments includes reducing the number of false alarms issued by a monitoring system. Physiological signals includes any signals that may be used to determine (e.g., calculate) a patient parameter. For example, light signals detected by a photodetector in a pulse oximeter may be used to calculate peripheral oxygen saturation (SpO2) data (e.g., the patient parameter). As such, the physiological signals may be signals used to detect vital signs or other parameters measured in a healthcare environment. However, the physiological signals may also be related to a position of the patient, movement of the patient, or images of the patient.

The physiological signals may be acquired by an acquisition device and communicated to a master unit. Data communicated between the acquisition device and the master unit is referred to as signal data. The signal data may be the physiological signals unchanged or the signal data may be based on or a function of the physiological signals. For example, the physiological signals may be converted into a signal form typically used in monitoring the patient parameter.

Types of data that may be acquired by embodiments set forth herein include heart rate data, blood pressure data, body temperature data, respiratory rate data, oxygen saturation data (e.g., SpO2 data), image data (e.g., still images, video images, and/or medical images), motion data (e.g., data from an accelerometer), position data (e.g., data from a global positioning system (GPS)), and electrical activity. The data of electrical activity may be, for example, electrocardiographic (ECG) data, cardiotocographic data, electroencephalographic (EEG) data, electromyographic data, or depth of sedation (DOS) data.

One or more embodiments may be or include a master unit. The master unit may be, for example, a central computing system (e.g., executing designated software) that analyzes signal data from multiple acquisition devices and/or other patient sources to make a decision on whether an alarm should be issued. As used herein, the term "alarm" includes any communication that is configured to alert or notify a healthcare provider that a health-related event has occurred. As used herein, a "health-related event" is any event that should be immediately or urgently (e.g., within a few minutes) brought to the attention of a healthcare provider so that the healthcare provider can decide whether and how to act. Such events are more important and urgent than general data collection. For example, although ECGs may be obtained by healthcare providers to assess the general heart health of a patient (e.g., during a follow-up appointment or check-up), ECGs may also be used to detect health-related events, such as a heart attack, that require immediate or urgent consideration or action. Health-related events typically occur in a hospital-like setting in which the patient is being monitored, but embodiments should not be limited to hospital-like settings. The health-related event may be related to a life threatening condition or otherwise potentially harmful condition of the patient.

The alarm communication may be a visual communication (e.g., flashing lights on a display, text message delivered to the wireless device of a healthcare provider, etc.), an audio communication (e.g., beeping sound or a recorded voice that broadcast to the healthcare provider), a tactile communication (e.g., shaking of handheld device), or a combination thereof. A single alarm may include multiple communications. For example, a communication delivered to the smartphone of a healthcare provider may cause the smartphone to beep and shake and for a text message to be displayed to the healthcare provider.

The data received and analyzed by the master unit may include data from acquisition devices (e.g., heart rate monitor, NIBP cuff, pulse oximeter, GPS device, or accelerometer). One or more of the acquisition devices may be capable of issuing an alarm independently. For example, the heart rate monitor may be capable of issuing an audible noise (e.g., beeping) or a visual flashing on a display when the heart rate is determined to be too low or too high. The data may also include data from other clinical sources, such as a patient file history, genetic history, etc.

An acquisition device may be directly connected through wires and cables to the master unit. Alternatively, the acquisition device may be wirelessly coupled to the master unit. The wireless communication may be in accordance with a wireless technology standard that is configured to exchange data over short distances (e.g., such as Bluetooth). However, a variety of communication standards may be used.

In some embodiments, one or more of the individual acquisition devices may communicate to the master unit that the acquisition device(s) has/have determined that an alarm should be issued. These acquisition devices may be referred to as "triggered acquisition devices." The determination by the triggered acquisition device may be made locally using circuitry of the acquisition device (referred to herein as device circuitry). For example, the triggered acquisition device may be hardwired to detect when the physiological signals have satisfied a designated condition, or the triggered acquisition device may have one or more processors configured to perform operations to detect when the physiological signals have satisfied a designated condition.

The master unit, taking into account different data than what the individual triggered acquisition device can provide, may decide whether to suppress issuance of the alarm of the acquisition device. In some embodiments, connectivity between the individual acquisition devices and the master unit is maintained and monitored. If the connection is compromised, the individual acquisition devices may be authorized to issue alarms without permission from the master unit. To this end, the acquisition devices may include an alarm or be communicatively coupled to an alarm. For example, the acquisition device may be capable of generating an audible noise and/or flashing one or more lights.

The master unit may use at least one of designated rules, algorithms, or artificial intelligence (AI) to analyze data available to the master unit to determine whether a warning signal provided by the acquisition device is clinically relevant or clinically irrelevant or unreliable. By way of example, an acquisition device may determine that the respiration rate of a patient exceeds a defined threshold. The acquisition device may communicate a warning signal to the master unit that indicates the defined threshold has been exceeded. In some cases, the acquisition device may confirm that a communication line is established between the acquisition device and the master unit. If the communication line has not been established or has been broken, the acquisition device may permit an alarm to be issued. For example, the acquisition device may generate the alarm of the acquisition device or communicate to another device to generate an alarm. The other device can be another acquisition device or another device that is capable of generating an alarm.

If the communication line between the acquisition device and the master unit exists and is functioning properly, the master unit may execute a designated protocol to determine whether the warning signal is clinically relevant or clinically irrelevant or unreliable. For instance, the master unit may execute a series of rule-based, algorithmic-based, and/or AI-based processes to determine whether the warning signal is clinically relevant or whether the warning signal is clinically irrelevant or unreliable.

To continue with the above example, the master unit may be communicatively coupled to a ventilator. After receiving the warning signal from the triggered acquisition device, the master unit may analyze other available data. For example, the master unit may be communicatively coupled to a ventilator in addition to the other device that detects the respiration rate. The ventilator may indicate that the respiration of the patient is normal. The master unit may determine that the warning signal is clinically irrelevant or unreliable because the respiration is normal. Optionally, the master unit may record or log any warning signals that were determined to be clinically irrelevant or unreliable.

To provide another example, a first acquisition device may be a heart rate monitor and the sensors may be the chest electrodes of the heart rate monitor. The heart rate monitor may determine that the heart rate has exceeded a designated threshold (e.g., 140 beats per minute (bpm)). The heart rate monitor may communicate a warning signal to the master unit. The warning signal may include, for instance, the detected heart rate and, optionally, the designated threshold. A second acquisition device may be a pulse oximeter. The pulse oximeter may communicate a pulse rate to the master unit. The pulse rate detected by the pulse oximeter may be, for example, 70 bpm. A third acquisition device may be a non-invasive blood pressure (NIBP) monitor. The NIBP monitor may communicate that the heart rate, when the last blood pressure measurement was acquired ten seconds ago, was 73 bpm. Based on the signal data from the pulse oximeter and the NIBP monitor, the master unit may determine that the warning signal from the heart rate monitor is clinically irrelevant or unreliable. In this example, the warning signal may have been caused by the electrodes being displaced or muscle activity (e.g., brushing teeth) and, as such, the physiological signals obtained by the electrodes are unreliable.

Embodiments may also determine whether the warning signal is clinically relevant or clinically irrelevant or unreliable by comparing a signal quality index (SQI) of the triggered acquisition device to the SQI of other acquisition devices. If an acquisition device has a higher SQI than other acquisition devices, embodiments may assign greater weight or importance to signal data from the acquisition device than signal data from other acquisition devices. In some embodiments, a warning signal or signal data from one acquisition device may be determined to be clinically relevant if the SQI of another acquisition device exceeds a threshold and the signal data from the other acquisition device indicates the warning signal or the signal data is clinically relevant. In some embodiments, a warning signal or signal data from one acquisition device may be determined to be clinically irrelevant or unreliable if the SQI of another acquisition device exceeds a threshold and the signal data from the other acquisition device indicates the warning signal or the signal data is clinically irrelevant or unreliable. In some embodiments, a warning signal or signal data from one acquisition device may be determined to be clinically relevant if the SQI of the acquisition device exceeds a threshold.

The signal data used to determine whether the warning signal is clinically relevant or clinically irrelevant or unreliable may have a direct relationship to the physiological signals of the triggered acquisition device. For example, the respiration rate detected by a first acquisition device may be compared to the respiration rate of a second acquisition device. However, the signal data used to determine whether the warning signal is clinically relevant or clinically irrelevant or unreliable may have an indirect relationship to the physiological signals of the triggered acquisition device. For example, as described above, a pulse rate may be used to determine whether the warning signal, caused by the heart rate exceeding a designated threshold, is clinically relevant or clinically irrelevant or unreliable. As another example, an accelerometer may indicate that a patient is moving when a warning signal is communicated by a triggered acquisition device. Because the patient is moving, the master unit may delay issuing an alarm until the master unit can confirm the warning signal is clinically relevant. As such, it should be understood that the signal data used to determine whether a warning signal is clinically relevant or clinically irrelevant or unreliable is not required to be derived from physiological signals that are the same type of physiological signals which caused the warning signal.

In some embodiments, the master unit may receive signal data from a primary acquisition device and signal data from at least one secondary acquisition device. As used herein, a "primary acquisition device" is the acquisition device that provides signal data that is primarily used to determine whether a health-related event has occurred. As used herein, a "secondary acquisition device" is an acquisition device that provides signal data for determining whether the signal data from the primary acquisition device is clinically relevant or whether the signal data is clinically irrelevant or unreliable.

As an example, the primary acquisition device may be an ECG monitor and one of the secondary acquisition devices may be an accelerometer. If the primary acquisition device provides signal data that is indicative of a health-related event occurring, the master unit may then determine the clinical relevance (or reliability) of the signal data from the primary acquisition device by analyzing signal data from the secondary acquisition device. If the master unit determines that the signal data from the primary acquisition device is clinically irrelevant or unreliable based on the signal data from the secondary acquisition devices, the master unit may suppress the patient alarm. If the secondary acquisition devices provide signal data that confirms the clinical relevance or reliability of the primary acquisition device, the master unit may permit the patient alarm to issue.

A patient alarm is "suppressed" if the patient alarm, based on the signal data of the primary (or triggered) acquisition device alone, would have normally occurred. In other words, the signal data (or warning signal) would have caused a patient alarm if it were not for the signal data from another acquisition device. In some embodiments, although the patient alarm is suppressed, another patient alarm may be issued that is different from the patient alarm that was suppressed. The other patient alarm may be, for example, less alarming to indicate that the information is clinically relevant, but may not be an emergency or urgent. For example, an embodiment may suppress a patient alarm that would have indicated that a patient's ECG data is consistent with a heart attack, but issue a less severe alarm so that a healthcare provider could check on the patient.

It should be understood that, in at least some embodiments, a positive determination as to whether the warning signal (or signal data) is clinically irrelevant or whether the warning signal (or signal data) is unreliable is not performed. In other words, determining whether a warning signal (or signal data) is "clinically irrelevant or unreliable" does not require further analysis to determine whether the warning signal (or signal data) is "clinically irrelevant" or whether the warning signal (or signal data) is "unreliable." The phrase "clinically irrelevant or unreliable" is a catch-all phrase that includes multiple possibilities and it may not be necessary to determine which possibility. Thus, for at least some embodiments, whether the warning signal (or signal data) is "clinically irrelevant" or whether the warning signal (or signal data) is "unreliable" is not important. In either case, a patient alarm may be suppressed.

In some embodiments, the patient monitoring system may be implemented in a tiered structure. For example, a local aggregation point of individual acquisition devices may exist in a patient room. Each of the acquisition devices may be managed by a master unit operating within the patient room. Alternatively, each of the acquisition devices may be managed by a master unit operating remotely (e.g., on the same level in a hospital or at another location entirely).

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. For example, one or more of the functional blocks (e.g., modules, processors, or memories) may be implemented in a single piece of hardware (e.g., a general purpose signal processor or random access memory, hard disk, or the like). Similarly, programs may be standalone programs, may be incorporated as subroutines in an operating system, may be functions in an installed software package, may be a software surface package that is run from a computer server remotely, and the like. It should be understood that the various embodiments are not limited to the arrangements and instrumentality shown in the drawings.

FIG. 1 is a block diagram of a patient monitoring system 100 (hereinafter "monitoring system") that is configured to monitor a patient. The monitoring system 100 includes a computing device or system 102 and a user interface 104 that is communicatively coupled to the computing system 102. The user interface 104 may include instruments (e.g., user display), hardware, and software (or a combination thereof) that permit the system 100 to display information to the user and, in some embodiments, permit the user to provide user inputs or selections. The user may be a healthcare provider, such as a doctor, nurse, or other suitably qualified individual. The user interface 104 may include an operator display 106 (e.g., monitor, screen, touchscreen, and the like) and an input device 108 (e.g., keyboard, computer mouse, tracking button, touchscreen, and the like) that is capable of receiving and communicating user inputs to the computing system 102. In some embodiments, a device constituting the input device 108 may also be the device constituting the operator display 106 (e.g., touchscreen). The user interface 104 may also be configured to query or prompt the user of the system 100 for designated information.

The computing system 102 may be integrated into one component (e.g., a laptop computer) or may be several components that may or may not be located near each other. The monitoring system 100 may include a master unit 105 and a plurality of acquisition devices 110. The master unit 105 has a processor 107 configured to execute programmed instructions stored in memory 109. Each of the acquisition devices 110 of said plurality of acquisition devices 110 may include one or more sensors (or transducers) 114 that are configured to detect physiological signals from the patient (not shown). Each of the acquisition devices 110 may also include device circuitry 112 that is configured to, among other things, determine whether the corresponding physiological signals satisfy a designated condition. The device circuitry 112 may also control operation of the acquisition device 110 and, optionally, convert the physiological signals into a different signal form. In FIG. 1, the acquisition device 110A is the triggered acquisition device or the primary acquisition device, as described below. The acquisition device 110B is the other acquisition device or the secondary acquisition device, as described below. In FIG. 1, a communication line 113 (double-headed arrow) exists between the acquisition devices 110 and the master unit 105 (or the computing system 102). The communication line 113 may be a physical line (e.g., wires or cables) and/or a wireless connection.

The device circuitry 112 may be, for example, hardwired circuitry that executes operations based on hard-wired logic that is configured to perform the algorithms and/or methods described herein. However, the device circuitry may be or include other processing circuitry that is configured to perform one or more tasks, functions, or steps, such as those described herein. The device circuitry 112 may be a logic-based device that performs operations based on instructions stored on a tangible and non-transitory computer readable medium, such as memory. The device circuitry 112 may include one or more ASICs and/or FPGAs. It is noted that the device circuitry 112 may not necessarily be limited to a single processor or a single hard-wired device. For example, the device circuitry 112 may include a single processor (e.g., having one or more cores), multiple discrete processors, one or more application specific integrated circuits (ASICs), and/or one or more field programmable gate arrays (FPGAs). In some embodiments, the device circuitry 112 is an off-the-shelf device that is appropriately programmed or instructed to perform operations, such as the algorithms described herein.

The device circuitry 112 may also include or be communicatively coupled to memory. In some embodiments, the memory may include non-volatile memory. For example, the memory may be or include read-only memory (ROM), random-access memory (RAM), electrically erasable programmable read-only memory (EEPROM), flash memory, and the like. The memory may be configured to store data regarding various parameters of the system.

In some embodiments, the device circuitry 114 may execute a set of instructions that are stored in one or more storage elements, in order to process the physiological signals and provide signal data. The storage elements may also store data or other information as desired or needed. The storage element may be in the form of an information source or a physical memory element within a processing machine. The set of instructions may include various commands that instruct the device circuitry 114 as a processing machine to perform specific operations such as the methods and processes described herein. Optionally, the set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine. The program is compiled to run on designated operating systems.

The sensors 114 are configured to detect physiological signals, such as from an individual (e.g., a patient), and communicate the physiological signals to the device circuitry 112, to the master unit 105, and/or to the computing system 102. For example, the sensors 114 may be electrodes configured to detect electrical activity within the patient, such as the electrical activity of the brain, heart, or other muscle. Alternatively or in addition to electrical activity, the sensors 110 may be configured to detect other physiological signals, such as a heart rate, body temperature, blood pressure, respiratory rate, intrauterine pressure, SpO2, etc. The physiological signals may be communicated to the device circuitry 112 and converted into the signal data. Alternatively, the physiological signals may be communicated directly to the master unit (e.g., in analog form). In such instances, the physiological signals may be referred to as signal data.

The computing system 102 may include or be part of a server system, a workstation, a desktop computer, a laptop computer, or a personal device, such as a tablet computer or a smartphone. However, the above are only examples and the computing system 102 may be other types of systems or devices. In the illustrated embodiment, the computing system 102 and/or the master unit 104 includes a system controller 116, which may comprise a controller, processor, or other logic-based device. The system controller 116 may have or be communicatively coupled to modules for performing methods as described herein.

In some embodiments, the computing system 102 may include or be communicatively coupled to one or more clinical sources 122. The other clinical sources 122 may include, for example, the Laboratory Information System (LIS), the Pharmaceutical Information System, the Electronic Medical Records (EMR), and/or the Physician Order Entry System. The clinical sources 122 may provide data regarding the patient that affects whether a warning signal is clinically relevant or clinically irrelevant or unreliable. The clinical sources 122 may store patient information that may be used to analyze a clinical relevance or reliability of the signal data received from the acquisition devices 110.

Non-limiting examples of data from clinical sources that may affect the designated conditions used by the master unit include recently administered medication. For example, a patient that has recently received beta-blocker for ST-depression. Beta-blockers may change the morphology of the ECG data. A vasopressor raises blood pressure and, as such, may change the designated conditions that determine whether an event has occurred. Data from a clinical source may also include computerized physician order entries (CPOEs). For example, a CPOE may provide instructions for applying therapy to a patient. The therapy may include repeatedly squeezing a patient's leg to reduce clotting. The repeated squeezing may affect some measurements. Other data may include data regarding a patient's metabolism or data regarding dietary changes. Yet another example is data regarding fluid management. The data may inform the master unit that boluses of saline solution have recently been provided to the patient, which may affect cardiac output.

Optionally, the monitoring system 100 may have a tiered structure that includes a plurality of computing systems 102 and/or master units 105. For example, each of the computing systems 102 may be located within a patient's room and be communicatively coupled to corresponding acquisition devices 110. The computing systems 102 may be communicatively coupled to a central system 120. The central system 120 may communicate with each of the computing systems 102. For example, the central system 120 may monitor a plurality of patients. The computing system 102, in such embodiments, may be referred to as a local aggregation system that manages the acquisition devices 110 in the patient's room.

Figure 2:
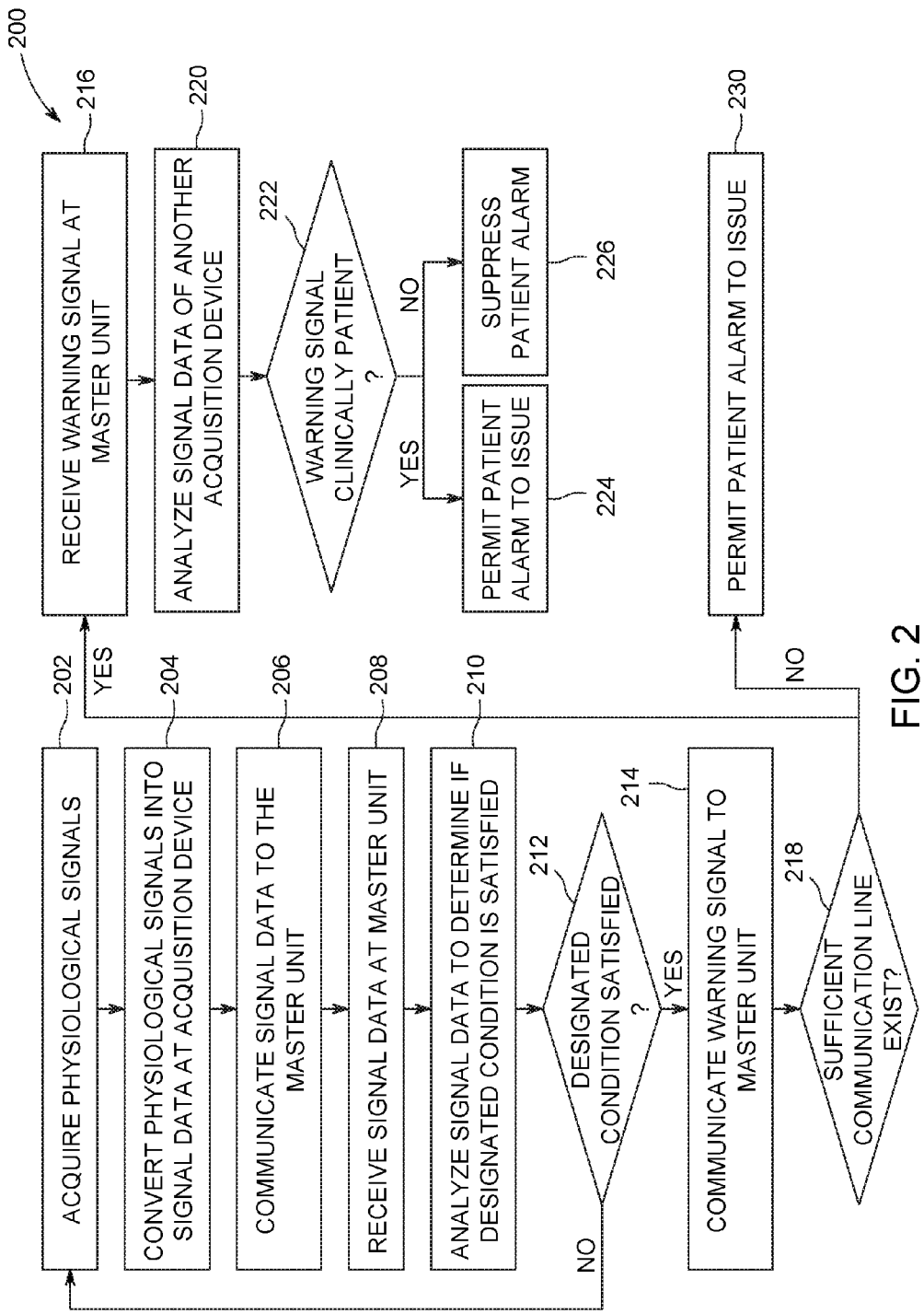
FIG. 2 is a flow chart illustrating a method of monitoring a patient in accordance with an embodiment.

FIG. 2 is a flow chart illustrating a method 200 formed in accordance with an embodiment. The method 200, for example, may employ structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion.

The method 200 includes acquiring, at 202, physiological signals from a patient. The patient may be human or other animal. The physiological signals may be suitable for determining (e.g., calculating) a patient parameter. For example, the physiological signals may be signals from a pressure sensor in an automated non-invasive blood pressure device. These signals may be used to calculate blood pressure. Optionally, the method 200 may include converting, at 204, the physiological signals to a form that is more suitable for determining the patient parameter. Using the above blood pressure example, the physiological signals may be converted into millimeters of Mercury (mm Hg). In particular embodiments, the converting, at 204, is performed by the device circuitry of the acquisition device. In other embodiments, the converting may be performed at the master unit.

Optionally, the signal data (e.g., the physiological signals or other converted signals) for at least one of the acquisition devices may be continuously, intermittently, or selectively communicated to the master unit at 206. The signal data may be automatically communicated to the master unit without a request by the master unit. Alternatively, the signal data may be communicated to the master unit only after receiving a request from the master unit. The signal data is received at the master unit at 208.

At 210, the signal data (e.g., the physiological signals or other converted signals) may be analyzed to determine whether the signal data satisfies a designated condition. The analysis, at 210, may be executed by the acquisition device or, in alternative embodiments, by the master unit. The designated condition may be whether the signal data has a value that is above an upper limit, below a lower limit, and/or within a designated value range. For example, if the signal data includes a heart rate, the value of the heart rate may be compared to upper and/or lower limits. In some embodiments, the designated condition may be applying the signal data to an algorithm. For example, an ECG may be analyzed using an algorithm to determine whether any of the waveforms in the ECG indicate a health-related event (e.g., long QT or ischemic event) has occurred.

At 212, the method may query whether the designated condition for identifying the occurrence of a health-related event has been satisfied. If the physiological signals (or signal data) does not satisfy the designated condition, at 210, the method 200 may return to acquiring the physiological signals. If the physiological signals (or signal data) does satisfy the designated condition, at 210, the acquisition device is a triggered acquisition device and the method 200 may then proceed to communicating, at 214, a warning signal to the master unit to which the triggered acquisition device is communicatively coupled. The warning signal may include the signal data (e.g., the physiological signals that caused the warning signal), the designated condition used, and other information. The warning signal effectively informs the master unit that the signal data from the triggered acquisition device indicates that a health-related event has occurred and, after confirmation, a patient alarm may be necessary. In some embodiments, the warning signal may only indicate that a health-related event has occurred without any specific data. The master unit receives the warning signal at 216.

During operation of the system and execution of the method 200, the acquisition devices may continuously, intermittently, or selectively communicate with the master unit to confirm that a sufficient communication line exists between the acquisition devices and the master unit. Prior to communicating the warning signal, at 214, or after attempting to communicate the warning signal, at 214, the method may query, at 218, whether a sufficient communication line between the acquisition device and the master unit exits. If a sufficient communication line does not exist, the method 200 may issue a patient alarm, at 230, that is indicative of a health-related event monitored by the triggered acquisition device. The patient alarm may be generated by the triggered acquisition device. Alternatively, the triggered acquisition device may communicate with an alarm device or system to generate the patient alarm. For example, the triggered acquisition device may be wirelessly coupled to speakers that generate a beeping noise.

If a sufficient communication line does exist, at 218, the warning signal is received by the master unit at 216. In response to receiving the warning signal from the triggered acquisition device, the master unit is configured to analyze, at 220, the signal data from another acquisition device of the plurality of acquisition devices to determine whether the warning signal is clinically relevant or clinically irrelevant or unreliable. As described above, the method may obtain the signal data of other acquisition devices throughout operation of the patient monitoring system. The signal data of the other acquisition device that is used to determine the clinical relevance or reliability of the signal data of the triggered acquisition device may: (a) be the same type of signal data obtained by the triggered acquisition device; (b) correspond to a patient parameter that is substantially related to the patient parameter of the signal data obtained by the triggered acquisition device; or (c) provide an explanation as to why the signal data of the triggered acquisition device may be clinically irrelevant or unreliable.

As to (a), signal data from two different acquisition devices are of the same type if the signal data corresponds to the same patient parameter. For example, a patient's heart rate may be determined by a variety of acquisition devices, such as an ECG monitor and an NIBP device. As to (b), a patient parameter determined by the signal data of one acquisition device is substantially related to a patient parameter determined by the signal data of another acquisition device if there is a known relationship between the two patient parameters such that one patient parameter may be used to estimate the other patient parameter (assuming the signal data from both acquisition devices is reliably acquired). For example, a pulse rate may be used to reliably estimate a heart rate and vice versa. In some embodiments, a reliable estimate is clinically relevant for determining whether a health-related event has occurred.

As to (c), signal data from another acquisition device may provide an explanation as to why the signal data of the triggered acquisition device is clinically irrelevant or unreliable if the signal data from the other acquisition device indicates why noise may exist within the signal data of the triggered acquisition device and/or why the acquisition device is not sufficiently coupled to the patient. For example, although the signal data from an ECG and accelerometer may typically not have a clinically relevant relationship, the accelerometer may indicate that the patient is moving and, as such, the ECG may not be clinically relevant.

At 222, the method may query whether the warning signal is clinically relevant or clinically irrelevant or unreliable. If the warning signal is clinically relevant, the method may, at 224, issue a patient alarm. The patient alarm may be associated with the triggered acquisition device. More specifically, the patient alarm may inform the healthcare provider as to which health-related event has occurred. The patient alarm may be communicated to a particular individual (e.g., text message to doctor) or may be generally communicated to a group of healthcare providers (e.g., beeping noise that could be heard by all people in a room). If the warning signal is clinically irrelevant or unreliable, the method may, at 226, suppress the patient alarm. The patient alarm that is permitted to issue at 224 may or may not be the same patient alarm that is permitted to issue at 230. Optionally, after suppressing the patient alarm at 226, the method may issue another patient alarm that is different than the patient alarm that was suppressed. The other patient alarm may indicate, for example, a less severe status of the patient than what would have been indicated by the patient alarm that was suppressed.

Figure 3:
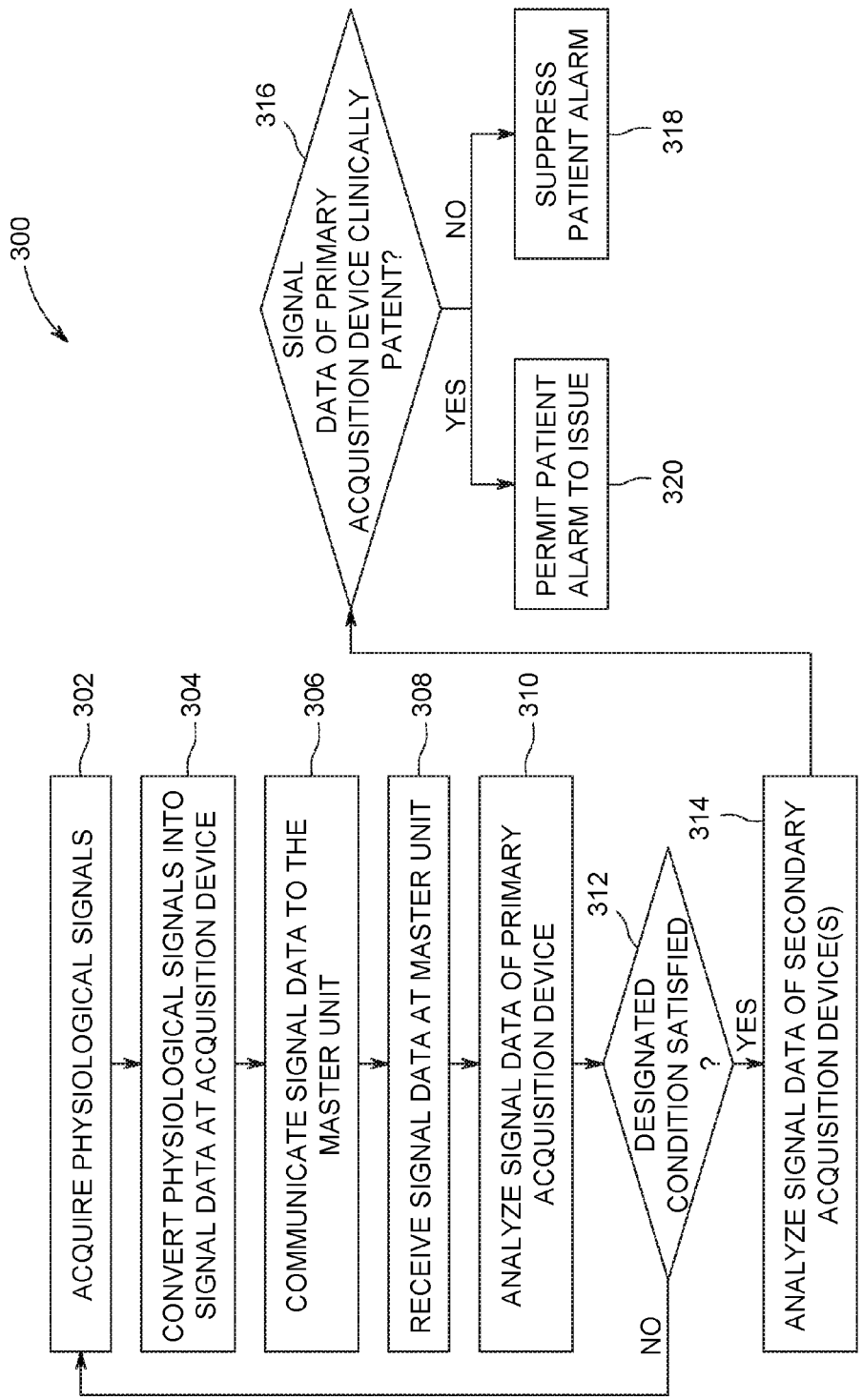
FIG. 3 is a flow chart illustrating a method of monitoring a patient in accordance with an embodiment.

FIG. 3 is a flow chart illustrating a method 300 formed in accordance with an embodiment. The method 300, for example, may employ structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion.

The method 300 may be similar to the method 200 (FIG. 2). For example, the method 300 includes acquiring, at 302, physiological signals from a patient. The physiological signals are obtained from a plurality of acquisition devices. Optionally, the method 300 may include converting, at 304, the physiological signals to a form that is more suitable for determining a patient parameter. Optionally, the signal data (e.g., the physiological signals or other converted signals) for at least one of the acquisition devices may be continuously, intermittently, or selectively communicated to the master unit at 306. The signal data may be automatically communicated to the master unit without a request by the master unit. Alternatively, the signal data may be communicated to the master unit only after receiving a request from the master unit. The signal data is received at the master unit at 308.

For various health-related events, the monitoring system may monitor the signal data of primary acquisition devices. As used herein, a "primary acquisition device" detects physiological signals that may be used to determine a patient parameter. The signal data from the primary acquisition device may be the most clinically relevant signal data for determining the patient parameter. For example, the heart rate may be most accurately determined by an ECG. When the patient parameter at issue is heart rate, the primary acquisition device may be the ECG monitor. It should be understood that, for embodiments in which multiple patient parameters are monitored, an acquisition device may be the primary acquisition device for one patient parameter but a secondary acquisition device for another patient parameter.

At 310, the signal data (e.g., the physiological signals or other converted signals) of the primary acquisition device may be analyzed to determine whether the signal data satisfies a designated condition. The analysis, at 310, may be executed by the master unit or, in alternative embodiments, by the acquisition device. As described above, the designated condition may be whether the signal data has a value that is above an upper limit, below a lower limit, and/or within a designated value range. For example, if the signal data includes a heart rate, the value of the heart rate may be compared to upper and/or lower limits. In some embodiments, the designated condition may be applying the signal data to an algorithm.

At 312, the method may query whether the designated condition for identifying the occurrence of a health-related event using the primary acquisition device has been satisfied. If the physiological signals (or signal data) does not satisfy the designated condition, at 310, the method 300 may return to acquiring the physiological signals. If the physiological signals (or signal data) does satisfy the designated condition, at 310, the method 300 may proceed to analyzing, at 314, the signal data of at least one secondary acquisition device. The secondary acquisition device provides signal data that may be used to determine whether the signal data of the primary acquisition device is clinically relevant or clinically irrelevant or unreliable. The analyzing, at 314, may be performed at the master unit.

During operation of the system and execution of the method 300, the acquisition devices may continuously, intermittently, or selectively communicate with the master unit to confirm that a sufficient communication line exists between the acquisition devices and the master unit. Prior to analyzing the signal data of the secondary acquisition devices, at 314, the method may confirm that a sufficient communication line exists with the secondary acquisition devices. If a sufficient communication line does not exist, the method may automatically issue a patient alarm. If a sufficient communication line does exist with the secondary acquisition devices, the method may proceed to analyzing, at 314, the signal data of the secondary acquisition devices.

As described above, the method may obtain the signal data of the primary and secondary acquisition devices throughout operation of the patient monitoring system. The signal data of the secondary acquisition device may be used to determine the clinical relevance or reliability of the signal data of the primary acquisition device. The signal data of the secondary acquisition device may: (a) be the same type of signal data obtained by the primary acquisition device; (b) correspond to a patient parameter that is substantially related to the patient parameter of the signal data obtained by the primary acquisition device; or (c) provide an explanation as to why the signal data of the primary acquisition device may be clinically irrelevant or unreliable.

At 316, the method may query whether the signal data from the primary acquisition device is clinically relevant or clinically irrelevant or unreliable. If the signal data from the primary acquisition device is clinically relevant, the method may, at 320, permit a patient alarm to issue. If the signal data from the primary acquisition device is clinically irrelevant or unreliable, the method may, at 318, suppress the patient alarm. Optionally, after suppressing the patient alarm at 318, the method may issue a patient alarm that is different from the suppressed alarm as described above.

In an embodiment, method of monitoring a patient is provided. The method includes receiving signal data of a patient from a plurality of acquisition devices that are operably coupled to the patient. The signal data is based on physiological signals detected by the acquisition devices. The method also includes analyzing the signal data of the primary acquisition device and at least one secondary acquisition device to determine whether a health-related event has been detected. Determining whether the health-related event has been detected includes determining whether the signal data from the primary acquisition device satisfies a designated condition associated with the health-related event. Determining whether the health-related event has been detected also includes, in response to determining that the signal data from the primary acquisition device satisfies the designated condition, determining whether the signal data from the at least one secondary acquisition device indicates the signal data of the primary acquisition device is clinically relevant or clinically irrelevant or unreliable. The method may include permitting a patient alarm to issue if the signal data from the at least one secondary acquisition device indicates the signal data of the primary acquisition device is clinically relevant. The method may include suppressing the patient alarm if the signal data from the at least one secondary acquisition device indicates the signal data of the primary acquisition device is clinically irrelevant or unreliable.

As used herein, the terms "computer" or "computing system" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer" or "computing system."

The computer or processor executes a set of instructions that are stored in one or more storage elements, in order to process input data and provide output data in the form of a health chart, among other things. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes described herein. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine. The program is compiled to run on designated operating systems.

As used herein, an element or step recited in the singular and proceeded with the word "a" or "an" should be understood as not excluding plural of said elements or steps, unless such exclusion is explicitly stated. For example, the phrase "a processor" may include a single processor, a multi-core processor, or a plurality of processors. If a plurality of processors are used, the plurality of processors may be found within a single unit (e.g., computer) or may be distributed throughout a system, such as in multiple units. If one processor is used, the claims may recite the processor as "only a single processor."

Furthermore, references to "one embodiment" are not intended to be interpreted as excluding the existence of additional embodiments that also incorporate the recited features. Moreover, unless explicitly stated to the contrary, embodiments that "comprise," "have," or "include" an element or a plurality of elements that have a particular property may also include additional such elements that do not have that particular property. Furthermore, when a feature is described as being based on a factor (e.g., signal data or physiological signals) or being a function of a factor, the term "based on" or "function of" should not be interpreted as the factor being the sole factor or primary factor, but may include the possibility that the element is also based on other factors.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A patient monitoring system comprising:
a plurality of acquisition devices, wherein the acquisition devices have sensors configured to detect physiological signals from a patient and device circuitry configured to determine whether the corresponding physiological signals satisfy a designated condition;
a master unit having a processor configured to execute programmed instructions stored in memory, the master unit configured to communicatively couple to the plurality of acquisition devices, the master unit, when executing the programmed instructions, configured to:
receive signal data of the patient from the acquisition devices, wherein the signal data is based on the physiological signals detected by one or more of the sensors of the corresponding acquisition devices;
receive a warning signal from a triggered acquisition device of the plurality of acquisition devices, the warning signal being communicated by the triggered acquisition device upon determining, at the triggered acquisition device, that the corresponding physiological signals of the triggered acquisition device satisfy the designated condition;
wherein, in response to receiving the warning signal from the triggered acquisition device, the master unit is configured to analyze the signal data from another acquisition device of the plurality of acquisition devices to determine whether the warning signal is clinically relevant or clinically irrelevant or unreliable, the master unit permitting a patient alarm associated with the triggered acquisition device to issue after determining the warning signal is clinically relevant, the master unit suppressing the patient alarm associated with the triggered acquisition device after determining that the warning signal is clinically irrelevant or unreliable;
wherein the triggered acquisition device is configured to confirm that a communication line exists between the triggered acquisition device and the master unit, the device circuitry of the triggered acquisition device causing the patient alarm to issue or another patient alarm to issue after determining that the communication line is insufficient for communicating the warning signal, the other patient alarm being indicative of a health-related event that is monitored by the triggered acquisition device.

2. The patient monitoring system of claim 1, wherein the master unit is configured to log the physiological signals of the triggered acquisition device when the warning signal was communicated and the signal data of the other acquisition device after determining that the warning signal is clinically irrelevant or unreliable.

3. The patient monitoring system of claim 1, wherein the signal data of the other acquisition device at least one of: (a) is the same type of signal data communicated by the triggered acquisition device; (b) corresponds to a patient parameter that is substantially related to the patient parameter of the signal data communicated by the triggered acquisition device; or (c) provides an explanation as to why the signal data of the triggered acquisition device is clinically irrelevant or unreliable.

4. The patient monitoring system of claim 1, wherein the signal data from the other acquisition device has a signal quality index and wherein the determination by the master unit as to whether the warning signal is clinically relevant or clinically irrelevant or unreliable is based on the signal quality index of the other acquisition device.

5. The patient monitoring system of claim 4, wherein the signal quality index is a first signal quality index, the signal data from the triggered acquisition device has a second signal quality index and wherein the determination by the master unit as to whether the warning signal is clinically relevant or clinically irrelevant or unreliable is based on the first and second signal quality indexes of the other acquisition device and the triggered acquisition device.

6. The patient monitoring system of claim 1, wherein the determination by the master unit as to whether the warning signal is clinically relevant or clinically irrelevant or unreliable is based on data from a clinical source, wherein the data from the clinical source changes the designated condition that was satisfied at the triggered acquisition device.

7. The patient monitoring system of claim 1, wherein the warning signal includes the signal data that caused the warning signal and additional data that instructs the master unit to issue the patient alarm.

8. A method of monitoring a patient, the method comprising:
communicatively coupling a master unit with a plurality of acquisition devices that are operably coupled to a patient, the acquisition devices having sensors configured to detect physiological signals from the patient and device circuitry configured to determine whether the corresponding physiological signals satisfy a designated condition, the acquisition devices being separate and distinct with respect to the master unit;
receiving, at the master unit, a warning signal from a triggered acquisition device of the plurality of acquisition devices, the warning signal being communicated by the triggered acquisition device upon determining, at the triggered acquisition device, that the corresponding physiological signals of the triggered acquisition device satisfy the designated condition, the warning signal informing the master unit that a patient alarm should be issued;
receiving, at the master unit, signal data from another acquisition device of the plurality of acquisition devices, the signal data being based on the physiological signals detected by the other acquisition device, and
analyzing at the master unit, in response to receiving the warning signal from the triggered acquisition device, the signal data from the other acquisition device to determine whether the warning signal is clinically relevant or clinically irrelevant or unreliable, wherein the method also includes permitting the patient alarm associated with the triggered acquisition device to issue after determining that the warning signal is clinically relevant or suppressing the patient alarm associated with the triggered acquisition device after determining that the warning signal is clinically irrelevant or unreliable: and
wherein the triggered acquisition device is configured to confirm that a communication line exists between the triggered acquisition device and the master unit, the device circuitry of the triggered acquisition device causing the patient alarm to issue or another patient alarm to issue after determining that the communication line is insufficient for communicating the warning signal, the other patient alarm indicative of a health-related event monitored by the triggered acquisition device.

9. The method of claim 8, wherein the warning signal includes the signal data that caused the warning signal and additional data that instructs the master unit to issue the patient alarm.

10. The method of claim 8, wherein the signal data from the other acquisition device has a signal quality index and wherein the determination as to whether the warning signal is clinically relevant or clinically irrelevant or unreliable is based on the signal quality index of the other acquisition device.

11. The method of claim 8, further comprising receiving data from a clinical source, wherein the determination as to whether the warning signal is clinically relevant or clinically irrelevant or unreliable is based on the data from a clinical source, wherein the data from the clinical source changes the designated condition that was satisfied at the triggered acquisition device.

12. The method of claim 8, wherein the acquisition devices are located in a patient room, the master unit being located outside of the patient room.

13. The method of claim 10, wherein the signal quality index is a first signal quality index, the signal data from the triggered acquisition device has a second signal quality index and wherein the determination by the master unit as to whether the warning signal is clinically relevant or clinically irrelevant or unreliable is based on the first and second signal quality indexes of the other acquisition device and the triggered acquisition device.

14. The method of claim 8, wherein determining, at the device circuitry, that the communication line is insufficient includes determining that the communication line is compromised.

15. A patient monitoring system comprising:
a plurality of acquisition devices having sensors configured to detect physiological signals from a patient;
a master unit having a processor configured to execute programmed instructions stored in memory, the master unit being separate and distinct with respect to the plurality of acquisition devices and configured to communicatively couple to the plurality of acquisition devices, the master unit, when executing the programmed instructions, configured to:
receive signal data of the patient from the acquisition devices, wherein the signal data is based on the physiological signals detected by the sensors of the corresponding acquisition devices, the acquisition devices including a primary acquisition device and one or more secondary acquisition devices;
analyze the signal data of the primary acquisition device and at least one secondary acquisition device to determine whether a health-related event has been detected, wherein determining whether the health-related event has been detected includes:
determining whether the signal data from the primary acquisition device satisfies a designated condition associated with the health-related event; and
in response to determining that the signal data from the primary acquisition device satisfies the designated condition, determining whether the signal data from the at least one secondary acquisition device indicates the signal data of the primary acquisition device is clinically relevant or clinically irrelevant or unreliable; and wherein a patient alarm is permitted to issue if the signal data from the at least one secondary acquisition device indicates the signal data of the primary acquisition device is clinically relevant, wherein the patient alarm is suppressed from issuing if the signal data from the at least one secondary acquisition device indicates the signal data of the primary acquisition device is clinically irrelevant or unreliable;

wherein the primary acquisition device has device circuitry configured to determine whether the corresponding physiological signals satisfy the designated condition, the primary acquisition device being permitted to cause the patient alarm to issue or another patient alarm to issue after determining that a communication line between the master unit and the primary acquisition device is insufficient and determining that the physiological signals have satisfied the designated condition, the other patient alarm indicative of the health-related event monitored by the primary acquisition device.

16. The patient monitoring system of claim 15, wherein the master unit is configured to log the signal data of the primary acquisition device and the at least one secondary acquisition device when the signal data from the at least one secondary acquisition device indicates the signal data of the primary acquisition device is clinically irrelevant or unreliable.

17. The patient monitoring system of claim 16, wherein the health related event is a first health-related event and the primary acquisition device is a first primary acquisition device, the master unit also configured to:

analyze the signal data of a different second primary acquisition device and at least one secondary acquisition device to determine whether a different second health-related event has been detected, wherein determining whether the second health-related event has been detected includes:

determining whether the signal data from the second primary acquisition device satisfies a designated condition associated with the second health-related event; and in response to determining that the signal data from the second primary acquisition device satisfies the designated condition, determining whether the signal data from the at least one secondary acquisition device indicates the signal data of the second primary acquisition device is clinically relevant or clinically irrelevant or unreliable.

18. The patient monitoring system of claim 17, wherein the second primary acquisition device is one of the secondary acquisition devices that provides signal data to determine whether the first health-related event occurred.

19. The patient monitoring system of claim 16, wherein the determination by the master unit as to whether the signal data from the primary acquisition device satisfies the designated condition associated with the health-related event is based on data from a clinical source.

20. The patient monitoring system of claim 19, wherein the data from the clinical source changes the designated condition associated with the health-related event.

* * * * *